United States Patent [19]

Kamiya et al.

[11] Patent Number: 4,822,127
[45] Date of Patent: Apr. 18, 1989

[54] MULTI-CHANNEL OPTICAL TRANSMISSION SYSTEM

[75] Inventors: Tadao Kamiya, Anaheim; Matthew J. Leader, Long Beach, both of Calif.

[73] Assignee: Shiley Incorporated, Irvine, Calif.

[21] Appl. No.: 874,919

[22] Filed: Jun. 16, 1986

[51] Int. Cl.$^4$ .............................................. G02B 6/26
[52] U.S. Cl. ................................ 350/96.15; 350/96.29
[58] Field of Search ............... 350/96.15, 96.16, 96.23, 350/96.29, 96.34

[56] References Cited

U.S. PATENT DOCUMENTS

| Re. 31,879 | 5/1985 | Lübbers et al. | 436/133 |
|---|---|---|---|
| 4,003,707 | 2/1976 | Lübbers et al. | 23/232 R |
| 4,041,932 | 8/1977 | Fostick | 356/39 |
| 4,200,110 | 4/1980 | Peterson et al. | 356/39 |
| 4,307,933 | 12/1981 | Palmer et al. | 350/96.16 |
| 4,465,335 | 8/1984 | Eppes | 350/96.21 |
| 4,474,431 | 10/1984 | Bricheno | 350/96.15 |
| 4,476,870 | 10/1984 | Peterson et al. | 128/634 |
| 4,548,907 | 10/1985 | Seitz et al. | 436/163 |
| 4,649,271 | 3/1987 | Hök et al. | 350/96.34 X |

FOREIGN PATENT DOCUMENTS

| 0147168 | 7/1985 | European Pat. Off. | 350/96.16 |
|---|---|---|---|
| 3036868 | 5/1982 | Fed. Rep. of Germany | 350/96.15 |
| 53-68249 | 6/1978 | Japan | 350/96.15 |
| 54-13347 | 1/1979 | Japan | 350/96.15 |
| 54-111363 | 8/1979 | Japan | 350/96.15 |

OTHER PUBLICATIONS

George E. Guilbault, "Practical Fluorescence" (1973)—pp. 599–600.

Primary Examiner—John D. Lee
Assistant Examiner—Phan T. Heartney
Attorney, Agent, or Firm—Peter C. Richardson; Lawrence C. Akers; Mark Dryer

[57] ABSTRACT

A multi-channel electromagnetic radiation transmission system comprising a plurality of first cladded optical fibers coupled to at least one second cladded optical fiber through a series of radiation-transmissible junctions each of which is encased in an opaque, radiation reflective jacket, and including means for attachment to radiation sensitive components whose emission signals are adapted to be received without substantial attenuation by a radiation measuring, transducing, recording or retransmitting component. A method for determining a plurality of parameters using such a system is also disclosed.

22 Claims, 3 Drawing Sheets

MULTI-CHANNEL OPTICAL TRANSMISSION SYSTEM

BACKGROUND OF INVENTION

This invention relates to a multi-channel electromagnetic radiation transmission system and particularly to a system which is adapted to be used in a plurality of modes for the selective determination of two or more substances in a medium. More particularly, the invention relates to a system involving a series of radiation-transmissible junctions of optical fibers, which system provides substantially unattenuated output radiation signals.

The invention is also concerned with a method for the determination of two or more parameters each of which is a function of the output radiation of a radiation sensitive component, utilizing said system.

The measurement of desired parameters in various media, particularly in biological systems, is frequently required. For example, the measurement in blood of pH levels and concentration of gases, particularly oxygen and carbon dioxide, is important during surgical procedures, post-operatively, and during hospitalization under intensive care and many devices for the measurement of said physiological parameters have been suggested in the art.

U.S. Pat. No. 4,003,707, Lubbers et al, and its reissue U.S. Pat. Re. No. 31,879, disclose a method and an arrangement for measuring the concentration of gases and the pH value of a sample, e.g. blood, involving the use of a fluorescent indicator at the end of a light-conducting cable which is sealingly covered by or embedded in a selectively permeable diffusion membrane. The radiation transmitted to and emitted from the indicator must be passed through various filtering elements and light elements, including reflectors, beam splitters and amplifiers before any meaningful measurements can be made.

U.S. Pat. No. 4,041,932, Fostick, discloses a method whereby blood constituents are monitored by measuring the concentration of gases or fluids collected in an enclosed chamber sealingly attached to a skin "window" formed by removing the stratum corneum over a small area of the patient's skin. The measurements in the enclosed chamber are made, inter alia, by determining the difference in intensity of light emitted from a fluorescent indicator.

U.S. Pat. Nos. 4,200,110 and 4,476,870, Peterson et al, disclose the use of a pH sensitive indicator in conjunction with a fiber optic pH probe. In each of these patents the dye indicator is enclosed within a selectively permeable membrane envelope.

U.S. Pat. No. 4,548,907, Seitz et al, discloses a fluorescent-based optical sensor comprising a membrane immobilized fluorophor secured to one end of a bifurcated fiber optic channel for exposure to the sample to be analyzed.

Many fluorescent indicators sensitive to pH, and thereby useful for $pCO_2$ measurements, are known in the art. Examples of useful fluorescent indicators are disclosed in the above patents and also in "Practical Fluorescence" by George E. Guilbault, (1973) pages 599–600.

Sensor devices using fluorescent indicators may be used for in vitro or in vivo determinations of components in physiological media. For in vitro determinations the size of the device is normally of no consequence, but for in vivo use, the size of the sensor may be extremely critical and there is an increasing need in the art to miniaturize sensor devices, particularly catheter-type devices, for the in vivo determination of components in physiological media, e.g. blood. However, diminution in size of the components of such devices, particularly in the size of the sensor itself, decreases the strength of the signal emitted by the indicator and consequently presents problems in the detection and measurement of said signal. These problems are aggravated when the detector system requires a multiplicity of components, such as filters, beamsplitters and reflectors to isolate and measure the emitted energy. Each of the said components reduces the emitted signal strength resulting in a sequential loss of measurable signal. Consequently, the more components present in the system, the weaker the final signal strength.

The problems associated with miniaturization of sensor devices are substantially solved by a device involving a radiation-transmissible junction of optical fibers encased in an opaque radiation reflective jacket as described and claimed in commonly assigned copending application No.

With the aid of said device the emission signal from radiation-sensitive indicators, particularly fluorescent indicators of the type disclosed in the prior art references discussed above, may be received substantially unattenuated in a suitable detector without the necessity of filters, beam splitters, reflectors or other light elements used in the prior art.

In accordance with the present invention the concept of retained signal strength embodied in the junction coupling device of the aforesaid copending application is further extended in a multi-channel system, capable of numerous modifications, for the determination of a plurality of parameters, while still retaining the advantage of optimal miniaturization without loss of signal strength.

SUMMARY OF THE INVENTION

In accordance with the present invention there is provided a multi-channel electromagnetic radiation transmission system comprising a plurality of first cladded optical fibers each having a proximal end and a distal end, said proximal end being adapted to receive radiation from a source and said distal end having an exposed tip which substantially contacts an exposed intermediate portion of a second cladded optical fiber having a proximal end and a distal end, the contact between said tip and said second optical fiber forming a radiation-transmissible junction which is encased in an opaque, radiation reflective jacket, said second cladded optical fiber being either a single fiber having a plurality of said junctions corresponding to the number of first optical fibers located sequentially along its length or one of a plurality of fibers each having at least one of said junctions, wherein the total number of said junctions corresponds to the number of first optical fibers, the proximal end of said single second optical fiber or of each of said plurality of second optical fibers being adapted to be attached to a radiation measuring, transducing, recording or retransmitting component and the distal end thereof being attached to a radiation sensitive component.

Each of the said junctions and its associated opaque, radiation reflective jacket is substantially the same as the junction and jacket claimed in copending application Ser. No. 874,927; and it is to be understood that no claim is made herein to the individual jacket and junction device per se. The present invention is concerned with a system in which a plurality of said devices is included as an essential component of a combination involving other components.

The present invention also provides a method for selectively determining a plurality of parameters each of which is a function of the output radiation of a radiation sensitive component, which comprises transmitting electromagnetic radiation from a source into a system comprising a plurality of first cladded optical fibers each having a proximal end and a distal end, said proximal end being adapted to receive said radiation and said distal end having an exposed tip which substantially contacts an exposed intermediate portion of a second cladded optical fiber having a proximal end and a distal end, the contact between said tip and said second optical fiber forming a radiation-transmissible junction which is encased in an opaque, radiation reflective jacket, said second cladded optical fiber being either a single fiber having a plurality of said junctions corresponding to the number of first optical fibers located sequentially along its length or one of a plurality of fibers each having at least one of said junctions, wherein the total number of said junctions corresponds to the number of first optical fibers, said source radiation entering the system through the proximal end of each of said plurality of first optical fibers, passing along each of said first optical fibers and through each of said junctions into said second optical fiber towards the distal end thereof, a major portion of any radiation not passing directly into said second optical fiber being internally reflected thereinto by its associated reflective jacket, impinging upon said radiation sensitive component attached to the distal end of said second optical fiber, causing said component to emit a signal having at least one characteristic dependent upon at least one of the parameters to be determined, and said signal passing substantially unattenuated through said second optical fiber toward the proximal end thereof whereby the desired determination is made with the aid of a radiation detector attached to the proximal end of said second optical fiber.

DETAILED DESCRIPTION OF THE INVENTION

In the system according to the invention the disposition of the second optical fiber with respect to each of the first optical fibers in each said radiation-transmissible junction is such that the output radiation from the radiation sensitive component attached to the distal end of said second optical fiber passes substantially unattenuated along said second optical fiber and through said junction to said measuring, transducing, recording or retransmitting component.

The preferred configuration is that in which the contact between said exposed tip of each said first optical fiber and said exposed intermediate portion of said second optical fiber is substantially parallel.

Furthermore, in a preferred embodiment the surface of the exposed tip in contact with the second optical fiber is pre-polished to flatness.

Each junction also provides a splitting of the source radiation into two components. A first, minor, component travels to the proximal end of the second optical fiber and the detector and a second, major, component travels to the distal end of the second optical fiber and the radiation-sensitive component. This provides a convenient means for source radiation compensation by measuring the ratio of the first component to the output radiation or emission signal.

According to the invention, the system may be arranged in a number of different ways and some of these arrangements will be particularly described as preferred embodiments. It is to be understood that numerous other arrangements are possible without departing from the spirit and scope of the invention, with the proviso that in every possible arrangement the signals reaching the detector must be discernable and measurable.

In one preferred embodiment of the invention the proximal end of each of said first optical fibers is attached to a separate source of electromagnetic radiation of a given wavelength.

In such an embodiment, it is also preferred that each of said first optical fibers is coupled through a said junction to a single second optical fiber, the distal end of which is attached to a single radiation sensitive indicator and the proximal end of which is attached to a detector adapted to disperse and measure the output radiation emitted by said indicator.

In another preferred embodiment the proximal ends of said plurality of first optical fibers are attached to a single source of electromagnetic radiation. In this embodiment it is also preferred that the distal end of each of said plurality of first optical fibers is coupled through a said junction to each of a plurality of said second optical fibers, the distal end of each of said second optical fibers is attached to a separate radiation sensitive indicator and the proximal ends thereof are attached to a radiation dispersing and measuring device.

Said radiation dispersing and measuring device preferably comprises a grating and a two dimensional array of radiation detectors. This type of device will be described in more detail hereinafter with reference to the accompanying drawings.

The optical fibers used in the system of the invention may be made of any suitable material which will transmit electromagnetic radiation of the desired wavelength. In a preferred embodiment each of said first and second cladded optical fibers is made of fused silica and the cladding is made of silicone. Fused silica is particularly suitable for the transmission of ultraviolet radiation.

Each of said first optical fibers and said second optical fiber may consist of a single fiber strand or a multiple fiber bundle. Preferably the exposed portion of said second fiber has a length equivalent to at least one fiber diameter.

The opaque, radiation reflective jacket which encases each of the radiation transmissible junctions of the system according to the invention effectively serves two functions; namely, to reflect any radiation which might otherwise escape from the junction back into the second optical fiber and to prevent any extraneous, unwanted radiation from entering the device. Thus, the jacket must be not only internally reflective, but also opaque with respect to external radiation. To accomplish this dual objective it is preferred that said jacket comprises an inner layer and an outer layer, said inner layer being made of a metal foil or a metalized film whose inner surface is coated with a film of reflective material and said outer layer being made of a heat-shrinkable, opaque, non-metallic material.

A preferred metal foil for said inner layer is aluminum foil. A preferred reflective material is barium sulfate.

Also, to enhance the coupling efficiency, it is desirable to apply a layer of optical coupling gel to the film of reflective material.

Said coupling gel is a standard material in the art having substantially the same refractive index as the material of the optical fibers. A typical example is a silicone gel.

The heat-shrinkable, opaque, non-metallic material preferably used as the outer layer of the jacket may be any material which is opaque to ambient radiation and which may be heat shrunk around the junction to form a radiation-tight seal. A suitable material is an opaque plastic, such as polyvinyl chloride. Preferably, to form a completely radiation-tight seal, the outer layer extends over and beyond the inner reflective layer and overlaps the cladded portion of each of the optical fibers.

In a preferred embodiment of the invention said radiation sensitive component attached to the distal end of the second optical fiber is at least one fluorescent indicator.

It is particularly preferred that the radiation sensitive component comprises a plurality of indicators each of which fluoresces upon excitation by the source radiation and each of which emits radiation of a different distinguishable wavelength, the intensity of each emitted signal being dependent upon the concentration of a substance under investigation.

A preferred source of radiation to be used with the system of the invention is a laser which produces controlled monochromatic or polychromatic radiation.

A further preferred embodiment is a system in which each of said first optical fibers is attached to a single polychromatic source of radiation and each of said fibers is associated with an optical filter which selects the wavelength and an optical relay which selects the timing of the radiation of a desired wavelength into said fiber. Preferably said optical relay comprises a component within said first optical fiber which controls the passage of excitation source radiation into said second optical fiber, which then acts as excitation radiation for an indicator species included in the radiation sensitive component attached to the distal end of said second optical fiber. The resulting system also preferably includes means for sequentially selecting one or more excitation radiation sources transmitted through said optical relays.

The system of the invention is particularly suitable for use in a method for selectively determining a plurality of parameters each of which is a function of the output radiation of a radiation sensitive component. A preferred embodiment of the method is one in which the parameters to be determined are the concentrations of at least two substances in at least one medium and said radiation sensitive component includes at least one fluorescent indicator whose emission radiation is dependent upon the presence of said substances. In such embodiment, preferably the signal emitted from each radiation sensitive component is dispersed and measured in a device comprising a grating and a two dimensional array of radiation detectors.

DESCRIPTION OF THE DRAWINGS

The invention will be more particularly described with reference to preferred embodiments of the system as illustrated in the accompanying drawings in which:

Referring to FIG. 1 of the drawings, the device, which is the subject of copending application No. comprises a first cladded optical fiber 1 having an exposed tip 2. The fiber is made of fused silica and the cladding 3 is made of radiation-opaque silicone.

Figure 1:
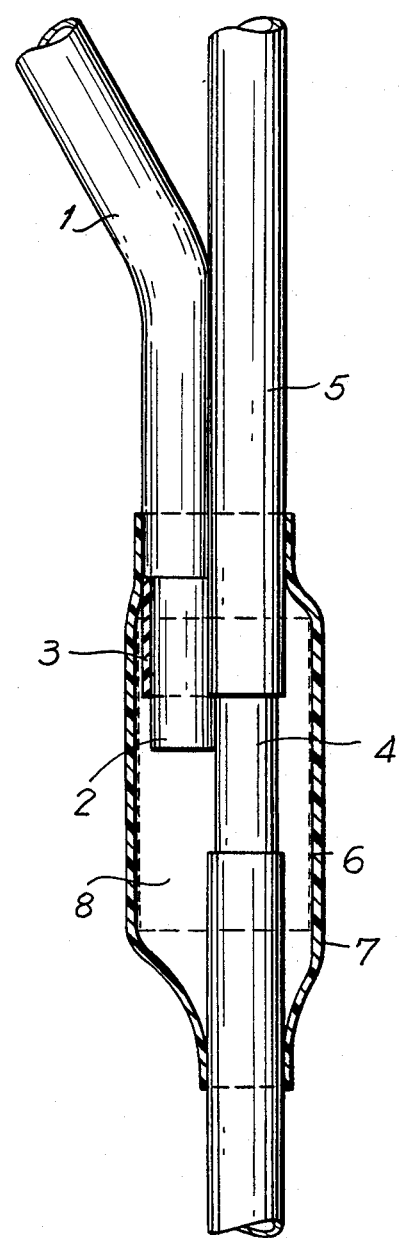
FIG. 1 is a schematic side elevation, partly in section, of a dual optical fiber device comprising a radiation transmissible junction encased in an opaque, radiation reflective jacket.
Figure 2:
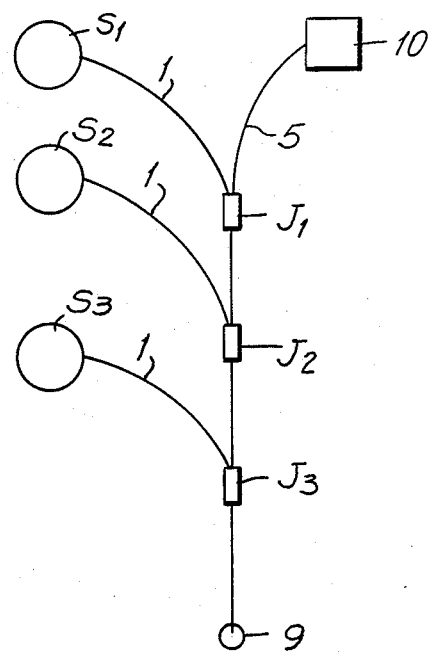
FIG. 2 is a schematic representation of one embodiment of the invention comprising three first optical fibers coupled to a single second optical fiber through three junctions located sequentially along the length of the second optical fiber.

The exposed tip of said first optical fiber is in substantially parallel contact with an exposed intermediate portion 4 of a second cladded optical fiber 5 made of the same materials as said first optical fiber.

The contact between said tip and said second optical fiber forms a radiation-transmissible junction which is encased in an opaque, radiation reflective jacket comprising an inner layer made of aluminum foil and illustrated schematically by dashed line 6 and an outer layer 7 made of a heat-shrinkable opaque non-metallic material, for example polyvinyl chloride. The maximum internal diameter of the opaque heat-shrinkable tubing is about 0.01 inch (0.025 mm) when used with a standard fused silica optical silica optical fiber of about 400 $\mu$m. diameter. Said outer layer extends beyond the inner metal foil layer and is heat shrunk onto both the inner layer and the cladding of the optical fibers to form a radiation-tight seal around the junction.

The aluminum foil 6 is coated on its inner surface, i.e. the surface facing the junction of the optical fibers, with a film of radiation reflective material, for example barium sulfate. A layer of index matching optical coupling gel, for example silicone gel, is applied to said film of reflective material. This layer substantially fills the space 8 between the reflective layer and the exposed optical fibers.

In one embodiment of the system according to the invention, a first junction $J_1$ as illustrated in FIG. 1 couples a first optical fiber 1 to a second optical fiber 5. Located sequentially along the second optical fiber are two further junctions $J_2$, $J_3$ which, in like manner, couple the second fiber to additional first optical fibers.

Each of said first optical fibers is adapted to receive radiation from sources $S_1$, $S_2$, $S_3$.

Attached to the distal end of the second optical fiber is a radiation sensitive component 9. This component contains fluorescent indicators adapted to be excited by radiation of wavelengths $\lambda_1$, $\lambda_2$ and $\lambda_3$ from sources $S_1$, $S_2$ and $S_3$, respectively. Upon excitation, said indicators emit fluorescent radiation, the intensity of which is dependent upon the concentration of the substances under investigation.

The emission signals from the radiation sensitive component 9 travel substantially unattenuated along the second optical fiber 5 to the proximal end thereof where they are dispersed and measured by an appropriate detecting device 10 attached to said proximal end.

Figure 3:
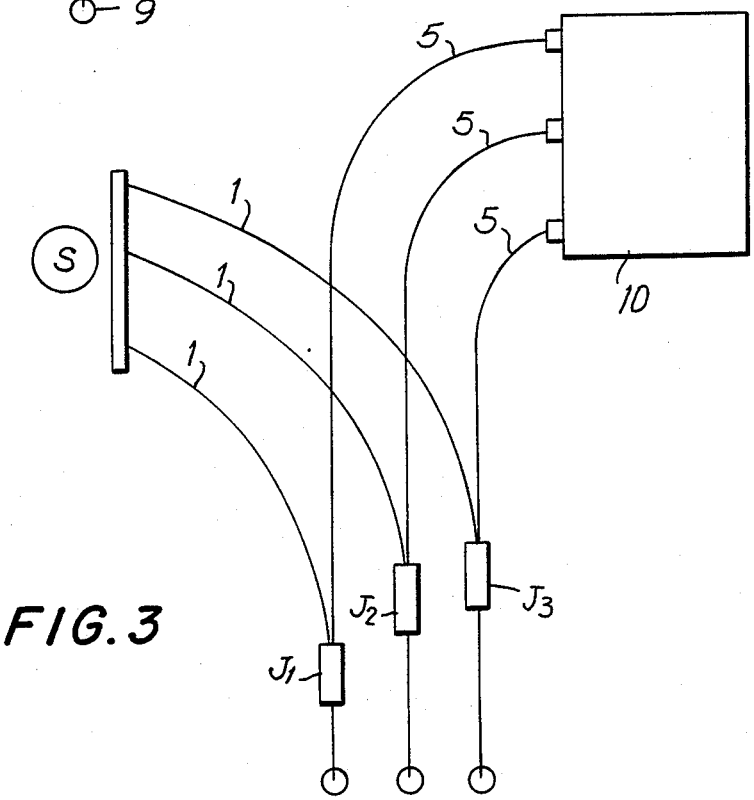
FIG. 3 is a schematic representation of another embodiment of the invention comprising three first optical fibers coupled through junctions to three second optical fibers.

The embodiment illustrated in FIG. 3 comprises three first optical fibers 1 adapted to receive radiation from a single source S.

Each of said first optical fibers is coupled through a junction $J_1$, $J_2$, $J_3$ to a separate second optical fiber 5.

Each second optical fiber has a radiation sensitive component 9 attached to its distal end.

The proximal end of each second optical fiber is attached to a terminal of a radiation dispersing and measuring device 10 which, in this embodiment, comprises a grating and a two dimensional radiation detector.

Figure 4:
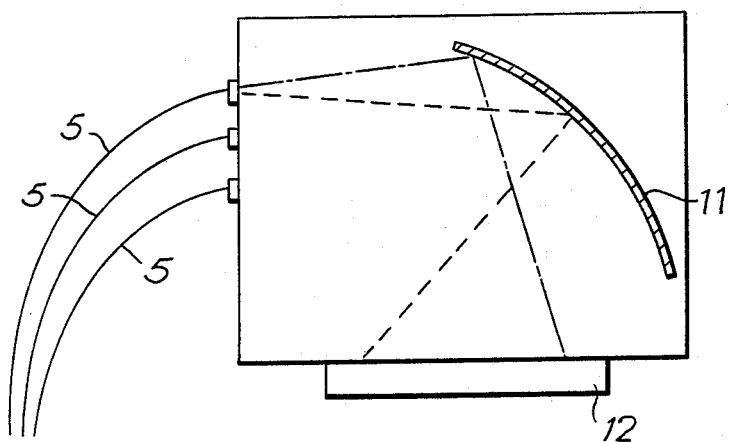
FIG. 4 is a schematic representation of a preferred radiation dispersing and measuring device comprising a grating and a two dimensional array of radiation detectors.
Figure 5:
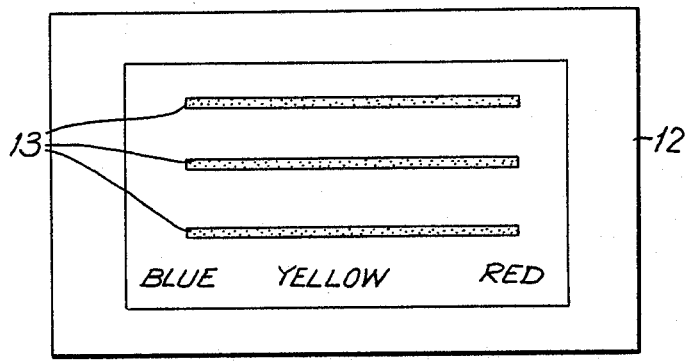
FIG. 5 illustrates the two dimensional array of FIG. 4.

As shown in FIG. 4, the signal from each second optical fiber is focussed by a concave holographic grating 11 onto a two dimensional array of radiation detectors 12.

Said array comprises a series of linear sequences of radiation detectors 13; each linear sequence being adapted to receive and measure the signal from one of said second optical fibers.

Thus each signal provides a visual spectrum which gives a quantitative determination of the parameter being measured.

The system of the invention provides high signal resolution and accurate quantitative determination of the parameters under investigation.

We claim:

1. A multi-channel electromagnetic radiation transmission system comprising a plurality of first cladded optical fibers each having a proximal end and a distal end, said proximal end being adapted to receive radiation from a source and said distal end having an exposed tip which touches but is not integrally joined to an exposed intermediate portion of a second cladded optical fiber having a proximal end and a distal end, the touch contact between said tip and the exposed portion of said second optical fiber forming a highly directional radiation-transmissible junction which is encased in an opaque, radiation reflective jacket, said second cladded optical fiber being either a single fiber having a plurality of said junctions corresponding to the number of first optical fibers located sequentially along its length or one of a plurality of fibers each having at least one of said junctions, wherein the total number of said junctions corresponds to the number of first optical fibers, the proximal end of said single second optical fiber or of each of said plurality of second optical fibers being adapted to be attached to a radiation measuring, transducing, recording or retransmitting component and the distal end thereof being attached to a radiation sensitive component, whereby the output radiation from said radiation sensitive component passes substantially unattenuated along said second optical fiber and through its associated junction toward the proximal end of said second optical fiber for determination by said radiation measuring, transducing, recording or retransmitting component.

2. A system according to claim 1, in which the proximal end of each of said first optical fibers is attached to a separate source of electromagnetic radiation of a given wavelength.

3. A system according to claim 2, in which each of said first optical fibers is coupled through a said junction to a single second optical fiber, the distal end of which is attached to a single radiation sensitive indicator and the proximal end of which is attached to a detector adapted to disperse and measure the output radiation emitted by said indicator.

4. A system according to claim 1, in which the proximal ends of said plurality of first optical fibers are attached to a single source of electromagnetic radiation.

5. A system according to claim 4, in which the distal end of each of said plurality of first optical fibers is coupled through a said junction to each of a plurality of said second optical fibers, the distal end of each of said second optical fibers is attached to a separate radiation sensitive indicator and the proximal ends thereof are attached to a radiation dispersing and measuring device.

6. A system according to claim 5, in which said radiation dispersing and measuring device comprises a grating and a two dimensional array of radiation detectors.

7. A system according to claim 1, in which the contact between the exposed tip of each of said first optical fibers and said exposed intermediate portion of said second optical fiber is substantially parallel.

8. A system according to claim 1, in which said first and second optical fibers are made of fused silica and the cladding is made of silicone.

9. A system according to claim 1, in which said jacket encasing each of said junctions comprises an inner layer and an outer layer, said inner layer being made of a metal foil or a metalized film whose inner surface is coated with a film of reflective material and said outer layer being made of a heat-shrinkable, opaque, non-metallic material.

10. A system according to claim 9, in which said metal foil is aluminum foil.

11. A system according to claim 9, in which said reflective material is barium sulfate.

12. A device according to claim 9, in which a layer of coupling gel is applied to said film of reflective material, and said layer substantially fills the space between said film of reflective material and the exposed optical fibers.

13. A system according to claim 1, in which said first optical fiber and said second optical fiber each consists of a single fiber strand or a multiple fiber bundle.

14. A system according to claim 1, in which said radiation sensitive component comprises at least one fluorescent indicator.

15. A system according to claim 14, in which the radiation sensitive component comprises a plurality of indicators each of which fluoresces upon excitation by the source radiation and each of which emits radiation of a different distinguishable wavelength, the intensity of each emitted signal being dependent upon the concentration of a substance under investigation.

16. A system according to claim 1, in which the source of radiation is a laser which produces controlled monochromatic or polychromatic radiation.

17. A system according to claim 1, in which each of said first optical fibers is attached to a single polychromatic source of radiation and each of said fibers is associated with an optical filter which selects the wavelength and an optical relay which selects the timing of the radiation of a desired wavelength into said fiber.

18. A system according to claim 17, in which said optical relay comprises a component within said first optical fiber which controls the passage of excitation source radiation into said second optical fiber, which then acts as excitation radiation for an indicator species included in the radiation sensitive component attached to the distal end of said second optical fiber.

19. A system according to claim 18 which includes means for sequentially selecting one or more excitation radiation sources transmitted through said optical relays.

20. A method for selectively determining a plurality of parameters each of which is a function of the output radiation of a radiation sensitive component, which comprises transmitting electromagnetic radiation from a source into a system comprising a plurality of first cladded optical fibers each having a proximal end and a distal end, said proximal end being adapted to receive said radiation and said distal end having an exposed tip which contacts an exposed intermediate portion of a second cladded optical fiber having a proximal end and a distal end, the contact between said tip and said second optical fiber forming a radiation-transmissible junction which is encased in an opaque, radiation reflective jacket, said second cladded optical fiber being either a single fiber having a plurality of said junctions corresponding to the number of first optical fibers located sequentially along its length or one of a plurality of fibers each having at least one of said junctions, wherein the total number of said junctions corresponds to the number of first optical fibers, said source radiation entering the system through the proximal end of each of said plurality of first optical fibers, passing along each of said first optical fibers and through each of said junctions into said second optical fiber towards the distal end thereof, a major portion of any radiation not passing directly into said second optical fiber being internally reflected thereinto by its associated reflective jacket, impinging upon said radiation sensitive component attached to the distal end of said second optical fiber, causing said component to emit a signal having at least one characteristic dependent upon at least one of the parameters to be determined, and said signal passing substantially unattenuated through said second optical fiber toward the proximal end thereof whereby the desired determination is made with the aid of a radiation detector attached to the proximal end of said second optical fiber.

21. A method according to claim 20, in which the parameters to be determined are the concentrations of at least two substances in at least one medium and said radiation sensitive component includes at least one fluorescent indicator whose emission radiation is dependent upon the presence of said substances.

22. A method according to claim 20, in which the signal emitted from each radiation sensitive component is dispersed and measured in a device comprising a grating and a two dimensional array of radiation detectors.

* * * * *